(12) United States Patent
Smith et al.

(10) Patent No.: US 10,682,041 B2
(45) Date of Patent: Jun. 16, 2020

(54) EXTENDIBLE FLEXIBLE SHEATH

(71) Applicant: Boston Scientific Scimed, Inc., Maple Grove, MN (US)

(72) Inventors: Paul Smith, Smithfield, RI (US); Barry Weitzner, Acton, MA (US); Robert B. Devries, Northborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 356 days.

(21) Appl. No.: 15/706,274

(22) Filed: Sep. 15, 2017

(65) Prior Publication Data

US 2018/0000322 A1 Jan. 4, 2018

Related U.S. Application Data

(63) Continuation of application No. 13/593,896, filed on Aug. 24, 2012, now Pat. No. 9,788,706.

(60) Provisional application No. 61/529,608, filed on Aug. 31, 2011.

(51) Int. Cl.
*A61B 1/00* (2006.01)

(52) U.S. Cl.
CPC ...... *A61B 1/00098* (2013.01); *A61B 1/00135* (2013.01); *A61B 1/00142* (2013.01)

(58) Field of Classification Search
CPC . A61B 1/00142; A61B 1/00135; A61B 1/018; A61B 1/00154; A61B 17/3431; A61B 2019/083
USPC .................................................. 600/121–125
See application file for complete search history.

(56) References Cited

U.S. PATENT DOCUMENTS

| 4,577,621 A | 3/1986 | Patel |
| 4,646,722 A | 3/1987 | Silverstein et al. |
| 5,630,782 A | 5/1997 | Adair |
| 5,817,015 A | 10/1998 | Adair |
| 5,916,145 A | 6/1999 | Chu et al. |
| 6,120,434 A | 9/2000 | Kimura et al. |

(Continued)

FOREIGN PATENT DOCUMENTS

| JP | H03-136630 A | 6/1991 |
| WO | 01/54567 A1 | 8/2001 |
| WO | WO 2010/111461 A1 | 9/2010 |

OTHER PUBLICATIONS

International Search Report and Written Opinion issued in PCT/US2012/052194, dated Mar. 13, 2014, 9 pages.

(Continued)

*Primary Examiner* — Alexandra L Newton
(74) *Attorney, Agent, or Firm* — Bookoff McAndrews, PLLC

(57) ABSTRACT

A sheath for a medical instrument includes an elongate body extending from a proximal end to a distal face. The elongate body may be configured to axially extend from a first length to a second length greater than the first length. The sheath may include a first hollow lumen extending from a first end proximate the proximal end to a second end proximate the distal face, and a second hollow lumen extending from the proximal end to the distal face. The second lumen may be open at the distal face. The sheath may also include a transparent window positioned at the second end of the first lumen to seal the first lumen at the second end. The transparent window may be configured to transmit light therethrough.

15 Claims, 9 Drawing Sheets

(56) References Cited

U.S. PATENT DOCUMENTS

| | | |
|---|---|---|
| 6,352,503 B1 | 3/2002 | Matsui et al. |
| 6,951,568 B1 | 10/2005 | Chin |
| 2002/0072652 A1 | 6/2002 | Berci et al. |
| 2003/0060680 A1 | 3/2003 | Wendlandt |
| 2003/0130564 A1 | 7/2003 | Martone et al. |
| 2004/0111009 A1 | 6/2004 | Adams et al. |
| 2005/0090709 A1* | 4/2005 | Okada ............... A61B 1/0005 600/104 |
| 2005/0222581 A1 | 10/2005 | Fischer, Jr. et al. |
| 2005/0272977 A1 | 12/2005 | Saadat et al. |
| 2006/0189845 A1 | 8/2006 | Maahs et al. |
| 2007/0112250 A1* | 5/2007 | Kura ............... A61B 1/00135 600/114 |
| 2007/0142709 A1 | 6/2007 | Martone et al. |
| 2007/0270646 A1 | 11/2007 | Weiner |
| 2008/0188869 A1* | 8/2008 | Weitzner ............. A61B 1/0014 606/130 |
| 2008/0193631 A1 | 8/2008 | Kanamori et al. |
| 2008/0221391 A1 | 9/2008 | Weitzner et al. |
| 2008/0243176 A1 | 10/2008 | Weitzner et al. |
| 2008/0249362 A1 | 10/2008 | Jiang et al. |
| 2009/0036739 A1 | 2/2009 | Hadani |
| 2010/0063358 A1 | 3/2010 | Kessler |
| 2010/0298642 A1* | 11/2010 | Trusty ............... A61B 1/00135 600/114 |
| 2011/0046442 A1 | 2/2011 | Matsushita |
| 2011/0118543 A1 | 5/2011 | Dosher et al. |
| 2011/0201889 A1 | 8/2011 | Vayser et al. |
| 2012/0316391 A1 | 12/2012 | Weitzner et al. |
| 2013/0053645 A1 | 2/2013 | Weitzner et al. |

OTHER PUBLICATIONS

International Preliminary Report on Patentability and Written Opinion issued in PCT International Application No. PCT/US2012/052195, dated Mar. 13, 2014, 9 pages.

International Search Report for International Patent Application No. PCT/US2012/052195, dated Nov. 29, 2012, 5 pages.

Weitzner, B., Smith, P., and Devries, R., Disposable Sheath with Lighting, U.S. Appl. No. 13/593,942, filed Aug. 24, 2012, 46 pages.

* cited by examiner

EXTENDIBLE FLEXIBLE SHEATH

CROSS-REFERENCE TO RELATED APPLICATIONS

This application is a continuation of U.S. application Ser. No. 13/593,896, filed on Aug. 24, 2012, which claims the benefit of priority under 35 U.S.C. § 119(e) of U.S. Provisional Application No. 61/529,608 to Smith et al. filed on Aug. 31, 2011, each of which is incorporated by reference herein in its entirety.

FIELD OF THE INVENTION

Embodiments of the present invention relate to an extendible flexible sheath for a reusable medical device. In particular, exemplary embodiments of the present invention relate to disposable extendible sheaths that allow reusable medical devices to be used within the body of a patient without direct tissue contact.

BACKGROUND OF THE INVENTION

Medical devices such as endoscopes and other similar medical instruments may be used for diagnostic and therapeutic applications within the body of a patient. While some of these instruments are disposable instruments that are discarded after a single use, others may be reusable. These reusable instruments have to be sterilized between uses to prevent cross contamination between patients. To reduce issues associated with sterilization and contamination, some of these reusable devices may be covered with sterile disposable sheaths during use. Such sheaths may be elongated, tubular components having a lumen for the insertion of the reusable medical device. During use, the sheath may isolate the reusable instrument from body tissue. After use, the disposable sheath is removed from the instrument and discarded. Since the reusable instruments themselves are not in contact with body tissue, the likelihood of contamination is minimized.

In some cases, it may be desirable to direct multiple medical instruments into the body to assist in a medical application. Some of these instruments may be disposable while others may be fully or partially reusable. Introducing these multiple instruments into the body individually may be inefficient and may also increase patient discomfort and trauma. To minimize patient discomfort and improve the efficacy of the medical procedure, it may be advantageous to direct these multiple instruments into the body through the same extendible disposable sheath. In these cases, it may be desirable to isolate the reusable instruments from the disposable instruments to minimize contamination. Embodiments of the current disclosure are directed to extendible flexible sheaths that enable multiple medical instruments to be used alongside each other within the body.

SUMMARY OF THE INVENTION

An embodiment of the invention discloses a sheath for a medical instrument. The sheath includes an elongate body extending from a proximal end to a distal face. The elongate body may be configured to axially extend from a first length to a second length greater than the first length. The sheath may include a first hollow lumen extending from a first end proximate the proximal end to a second end proximate the distal face, and a second hollow lumen extending from the proximal end to the distal face. The second lumen may be open at the distal face. The sheath may also include a transparent window positioned at the second end of the first lumen to seal the first lumen at the second end. The transparent window may be configured to transmit light therethrough.

Various embodiments of the invention may include one or more of the following aspects: a third lumen extending from the proximal end to the distal face, the third lumen being open at the distal face; the elongate body may include a diverging element positioned proximate the distal face, wherein activation of the diverging element enables the second lumen and the third lumen to diverge from each other at the distal face; the elongate body may further include an extendible section that is configured to extend and increase a length of the elongate body from the first length to the second length; the extendible section may be positioned proximate the proximal end of the elongate body and the first and the second hollow lumens may extend through the extendible section; the extendible section may include a tubular structure capable of being axially expanded and contracted in a bellows-like fashion; the extendible section may be activated using a control mechanism positioned at a proximate end of the medical instrument; the sheath may include a neck region that extends from the distal face to the second end, at least a portion of the first lumen may be being positioned in the neck region; the neck region may include an extendible section that is configured to axially extend to increase a length of the neck region; the neck region may be configured to axially extend and contract upon application of an axial force; and the neck region may be adapted to axially extend and contract in a bellows-like fashion.

An embodiment of the invention discloses a medical device including a flexible sheath extending from a proximal end to a distal face. The flexible sheath may include an extendible section configured to axially extend from a first length to a second length greater than the first length. The flexible sheath may include a first hollow lumen that extends through the flexible sheath from the proximal end to the distal face. A neck region may extend the first lumen from the distal face of the sheath to a second end that is distal to the distal face of the sheath. The first lumen may be closed at the second end by a transparent window. A second hollow lumen may extend from the proximal end to the distal face of the sheath. The second lumen may be open at the distal face.

Various embodiments of the invention may include one or more of the following aspects: a third lumen extending from the proximal end to the distal face of the flexible sheath, the third lumen may be open at the distal face and extend through the extendible section; the extendible section may be positioned proximate the proximal end of the flexible sheath and the first and the second hollow lumens may extend through the extendible section; the extendible section may be configured to axially extend and contract in a bellows-like fashion; the first length of the extendible section may be about 4 cm and the second length of the extendible section may be about 220 cm; and the neck region may include an extendible section that is configured to axially extend to increase a length of the neck region.

An embodiment of the invention may disclose a method of using a medical device. The method may include inserting a distal end of a sheath into the body of a patient. The sheath may include an elongate body extending from a proximal end to the distal end and a first lumen extending therethrough. The first lumen may be closed at the distal end by a transparent window. The method may also include inserting a first medical instrument having an optical device into the first lumen of the sheath either before, during, or after the sheath is inserted into the body. The method may also include exerting an axial force on the sheath to axially extend the sheath from a first length to a second length greater than the first length. The method may further include positioning the optical device of the first medical instrument proximate the transparent window.

Various embodiments of the method may include one or more of the following aspects: inserting a second medical instrument through a second lumen of the sheath to extend an end effector of the second medical instrument out of the distal end of the sheath; applying a second axial force on the sheath to axially extend the sheath relative to the end effector of the second medical instrument; and activating the optical device of the first medical instrument to transmit light through the transparent window.

BRIEF DESCRIPTION OF THE DRAWINGS

The accompanying drawings, which are incorporated in and constitute a part of this specification, illustrate embodiments of the invention and together with the description, serve to explain the principles of the invention.

It should be noted that the dimensions of the assemblies shown in the figures may be distorted for clarity of the illustration, and different proportions of the different dimensions are also possible, and like reference numbers in different figures represent similar elements.

DESCRIPTION OF THE EMBODIMENTS

Reference will now be made to exemplary embodiments of the invention, examples of which are illustrated in the accompanying drawings. Wherever possible, the same reference numbers will be used throughout the drawings to refer to the same or like parts. The terms "proximal" and "distal" are used herein to refer to the relative positions of a device. As used herein, "proximal" refers to a position relatively closer to the exterior of the body or closer to a user using the device. In contrast, "distal" refers to a position relatively further away from the user using the device or closer to the interior of the body.

Figure 1:
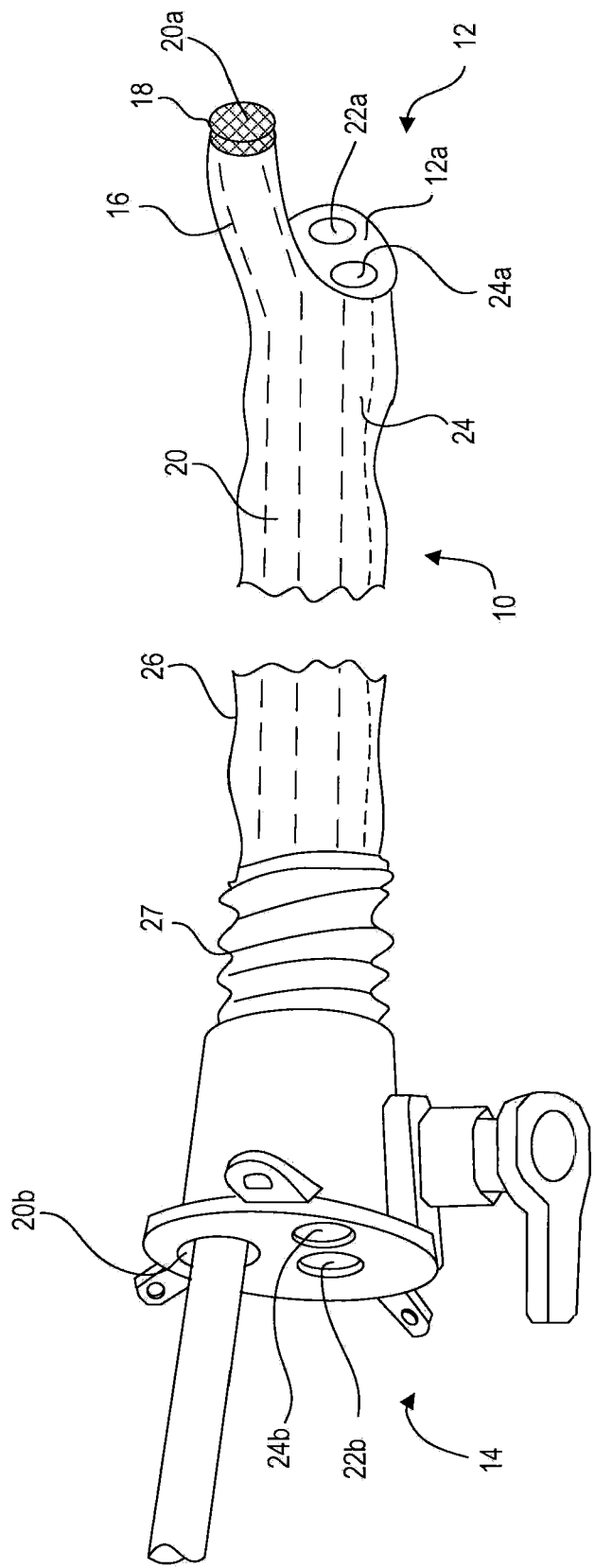
FIG. 1 is a schematic view of an exemplary embodiment of a sheath of the current disclosure.

FIG. 1 depicts an exemplary guide or sheath 10 of the current disclosure. Sheath 10 may include a flexible elongate body 26 that extends between a proximal end 14 and a distal end 12. During application, the distal end 12 may be positioned within the body of a patient while the proximal end 14 may extend outside the body. The distal end 12 of the sheath 10 may be inserted into the body of the patient and extended into the body (such as, for example, through a body tract) to position the distal end 12 at a desired work site within the body. The sheath 10 may be inserted into the body transluminally, intraluminally, percutaneously or by any other means. For example, the distal end 12 of sheath 10 may be inserted into the body of a patient through the mouth and extended into the body through the esophagus to position the distal end 12 proximate an ulcer on the stomach wall, while the proximal end 14 is positioned outside the body. Elongate body 26 may be flexible so as to enable the sheath 10 to bend and pass through tortuous body tracts as the distal end 12 advances into the body through the body tract. In some embodiments, an external surface of elongate body 26 may be made of, or coated with, a polymeric or a lubricious material (such as, for example, MDX coating, PTFE extrusions, etc.) to enable the sheath 10 to pass through body cavities with ease. It is also contemplated that, in some embodiments, an external surface of the elongate body 26 is coated with (or provided with) medicines (such as, antibiotics, etc.) to assist in healing. In some embodiments, elongate body 26 may have surface modifications to ease insertion and extraction into the body.

The elongate body 26 may include an extendible section 27 along its length. The extendible section 27 may enable the elongate body 26 to extend in length from a relatively short length to a substantially longer length. In some embodiments, the extendible section 27 may extend along substantially the entire length of elongate body 26, while in other embodiments, the extendible section 27 may only extend along a segment of elongate body 26. In one embodiment, the extendible section may be positioned between a proximal handle of sheath 10 and a more flexible portion of elongate body 26. In some embodiments, a material of the extendible section 27 may be different from, and/or more flexible than, a material of the remainder of the elongate body 26. Alternatively or additionally, the extendible section 27 may be constructed in a manner that permits the extendible section 27 to extend in length. The extendible section 27 may have any length and may extend to any length. In some embodiments, in an extended state, the extendible section 27 may only be a few inches or less in length, while in other embodiments, it may be longer. In general, the extendible section 27 may be positioned anywhere along the length of the elongate body (for example, in a distal portion, a proximal portion, a medial portion, etc.). In some embodiments, multiple extendible sections 27 may be positioned in different portions of the elongate body.

Extendible section 27 may include any arrangement that enables the elongate body 26 to extend axially from a relatively short length to a longer length. In some embodiments, a tubular bellows-like member capable of being axially expanded and contracted may be used as the extendible section 27. In some embodiments, a flexible material may be wrapped around the outside of a helical supporting member that is axially extendible. The flexible material may have sufficient axial slack to permit lengthwise extension of the elongate body 26. In some embodiments, the extendible section 27 may have overlapping telescoping sections that unfold and extend during use. In some embodiments, the extendible section 27 may be a covered mechanically extendible section, such as, for example, a covered stent, that can expand and contract during use. In some embodiments, the extendible section 27 may be a region of high elasticity (such as, for example, one or more rings or high elasticity) compared to other portions of the elongate body 26. Applying a force on the elongate body 26 (such as, for example, by pushing using an instrument passing through a lumen of the elongate body 26) in an axial direction may extend the length of the extendible section 27, thereby enabling the elongate body 26 to extend from a first length to a second length. Applying a force in the opposite direction may axially compress the extendible section 27, thereby compressing the elongate body 26 from the second length to the first length. In general, the first length and the second length may have any values. For instance, in some embodiments, the first length may be about 4 cm and the second length may be about 220 cm. The extendible section 27 may enable the length of sheath 10 to be changed as needed based on a location of the treatment site relative to the body opening. The extendible section 27 may also enable the proximal end 14 of the sheath 10, including any handle portion and insertion ports, to be located close to the body opening (a natural body opening such as anus, mouth, etc., or a surgical incision).

The extendible section 27 may be extended and contracted (activated) in any manner. In some embodiments, the extendible section 27 may be activated manually, while in other embodiments, linking members, such as, for example, control wires (or other devices) may couple the extendible section 27 to the proximal end 14 of the sheath 10 thereby enabling the extendible section 27 to be activated from the proximal end 14 of sheath 10. It is also contemplated that, in some embodiments, the extendible section 27 may be activated in another manner, such as, for example, thermally or electrically.

One or more lumens (such as, for example, first lumen 20, second lumen 22, and third lumen 24) may extend through the elongate body 26 from the proximal end 14 to the distal end 12. In general, any number of lumens may extend through the elongate body 26. While one or more of these lumens may be sealed at the distal end 12 to prevent the entry of biological fluids thereinto, the other lumens may be open. For instance, first lumen 20 may be sealed at the distal end 12 as illustrated in FIG. 1. An optically transparent window (such, as for example, a viewing lens 18) may be provided at the distal end 12 of first lumen 20 to allow light to pass therethrough, while isolating the interior of first lumen 20 from body tissue and fluids. Any type of material that allows at least a portion of light to pass therethrough may be used as viewing lens 18. Viewing lens 18 may incorporate features such as, magnification, filtering, polarizing, etc. During application, a reusable medical instrument (such as, for example, the reusable instrument 50 discussed with reference to FIGS. 3A and 3B) may be directed into the body through first lumen 20. This reusable instrument may be inserted into the first lumen 20 through an opening 20b at the proximal end 14 of the sheath 10. The reusable instrument may then be pushed into the sheath 10 through the first lumen 20 to position its distal end proximal to the viewing lens 18. Pushing the reusable instrument into the first lumen 20 may provide the force necessary to extend the extendible section 27. In some embodiments, the distal end of the first lumen 20 may include features that may mate with corresponding features on the distal end of the reusable instrument to position the reusable instrument in a suitable manner at the distal end of the sheath 10.

In some embodiments, as illustrated in FIG. 1, at the distal end 12, the first lumen 20 may include a protruding neck region 16 that extends past a distal face 12a of the sheath 10. In these embodiments, the distal-most end 20a of the first lumen 20 may be longitudinally displaced from the distal face 12a, and viewing lens 18 may be provided at the distal-most end 20a. The protruding neck region 16 may be configured to deflect with respect to the distal face 12a of the sheath 10.

As opposed to the first lumen 20 which is closed at the distal end 12 and open at the proximal end 14, the second lumen 22 and the third lumen 24 may be open at both the proximal end 14 and the distal end 12. A medical instrument or device may be inserted into the second and the third lumens 22, 24 through openings 22b, 24b at the proximal end 14. These instruments may then be pushed into sheath 10 to extend the distal ends of the instruments into the body through openings 22a, 24a at the distal end 12 of sheath 10. The second lumen 22 and the third lumen 24 may provide access for medical instruments that may aid in performing any desired medical procedure within the body. Although the distal ends of the second and third lumens 22, 24 are described as being open, in some embodiments, the openings 22a, 24a at the distal ends of these lumens may include seals or other devices that may prevent or decrease the entry of biological fluids into the lumens while allowing a medical instrument to pass therethrough. These seals may be active or passive seals. In some embodiments, a distal end of a medical instrument inserted through the second and third lumens 22, 24 may penetrate or pierce through a seal to extend out of the distal end of the lumen. The seal may snugly fit around a portion of the instrument that extends out of the lumen to prevent or minimize the entry of biological fluids into the lumen.

Sheath 10 may be made of any material (metal, plastic, polymeric, etc.) and have any stiffness (of flexibility) to suit an application. In some embodiments, the sheath 10 may be a relatively floppy component, while in other embodiments the sheath 10 may be relatively rigid. It is also contemplated that, in some embodiments, selected portions of the sheath 10 may be relatively rigid while other portions may be relatively flexible. The increased rigidity at the selected portions may be provided by incorporating different materials into the sheath 10 or by incorporating features (stiffening ribs, thicker regions, etc.) that impart rigidity to selected regions of the sheath 10. In some embodiments (such as, for example, when sheath 10 is relatively floppy), an instrument may be inserted into a lumen of the sheath 10 before the sheath 10 (along with the inserted instrument) is inserted into the body of the patient. In such an embodiment, the stiffness provided by the inserted instrument may guide the sheath 10 into the body. After the sheath 10 is appropriately positioned within the body, other instruments may be inserted through other lumens of the sheath 10. For example, in one exemplary embodiment, a reusable instrument may be inserted into the sealed first lumen 20 of a relatively floppy sheath 10 before the sheath 10 is inserted into a body cavity. Once the distal end 12 of the sheath 10 is appropriately positioned in the body, the disposable instruments may be inserted through the second and third lumens 22, 24. It is also contemplated that disposable instruments are also inserted into the sheath 10 before the sheath 10 is inserted into the body cavity.

In some embodiments, sheath 10 may be inserted into the body and positioned at a desired location in the body before the disposable and reusable instruments are inserted into the lumens of the sheath 10. In such an embodiment, the inserted sheath 10 acts as a guide to direct the instruments into the body. It is also contemplated that, in some embodiments, one or more instruments or guides may be inserted into the body, and the sheath 10 may be slid over the inserted instrument from the proximal end of the instrument. For example, in some exemplary applications, an instrument may first be inserted into the body (individually inserted or inserted through a guide tube, etc.). The proximal end of the inserted instrument (located outside the body) may be inserted into the distal end of the sheath (through an open lumen), and the sheath 10 pushed into the body until the distal end 12 is positioned at a desired location within the body. In such an embodiment, the inserted instrument may guide the sheath 10 to the desired location in the body. Once positioned at the desired location, the reusable instrument may then be inserted through the sealed first lumen 20.

Figure 2A:
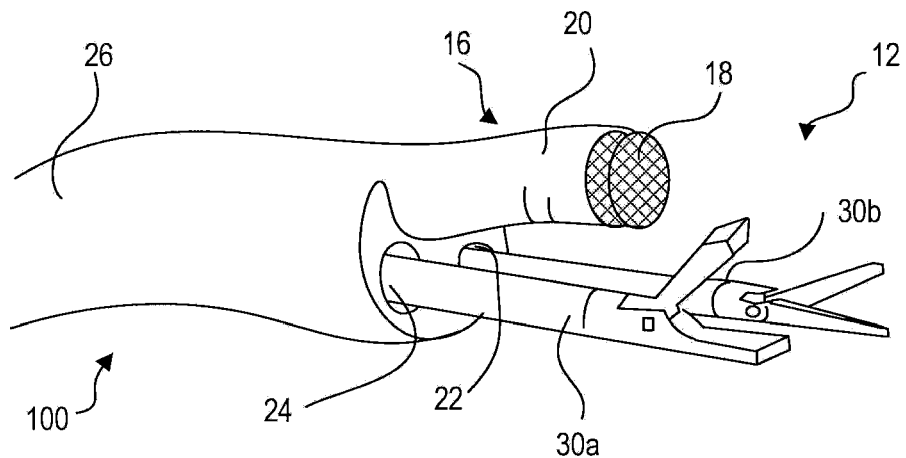
FIG. 2A is a schematic view of the distal end of exemplary sheath of the current disclosure.
Figure 2B:
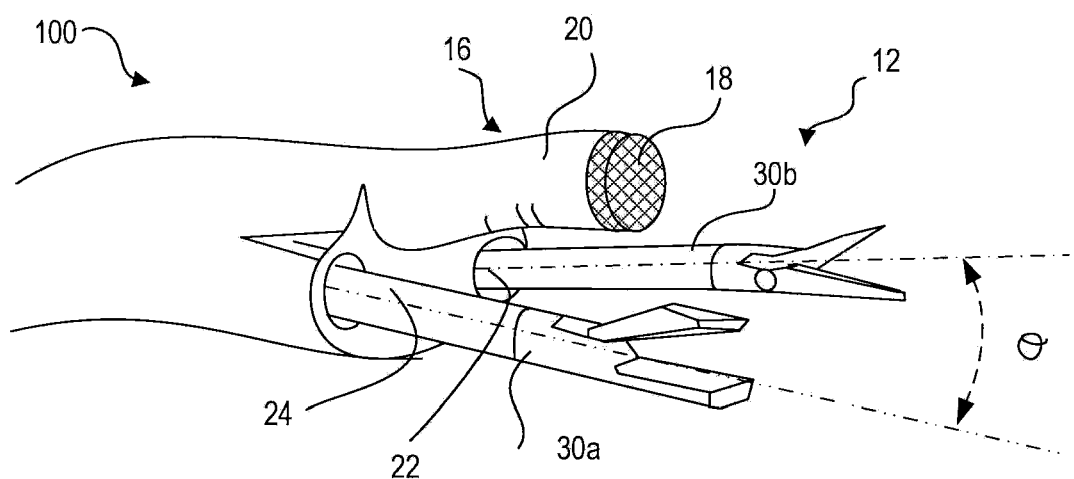
FIG. 2B is a schematic view of the distal end of the sheath of FIG. 2A post activation of the diverging element of the sheath.

In some embodiments, as illustrated in sheath 100 of FIGS. 2A and 2B, a diverging element 28 may be included in the elongate body 26 to enable instruments 30a and 30b in the second and third lumens 22, 24 to diverge from each other at the distal end 12. FIG. 2A illustrates a view of sheath 100 before diverging element 28 is activated, and FIG. 2B illustrates a view of the sheath 100 after the activation of diverging element 28. These diverging elements 28 may include both active and passive devices. Activation of the diverging element 28 may enable the ends of the instruments 30a, 30b that extend out of the second and third lumens 22, 24 to diverge from each other by any angle θ. Although FIGS. 2A and 2B illustrate the instruments 30a and 30b in the second and third lumens 22, 24 as diverging only from each other, in some embodiments, the diverging element 28 may also be configured to enable these instruments 30a, 30b to diverge from the distal end of the reusable instrument in the first lumen 20 also. Although the diverging element 28 may be positioned at any location in sheath 100, in some embodiments, the diverging element 28 may be positioned proximate the distal end 12 of the sheath 100 to enable the distal ends of the instruments delivered through sheath 100 to diverge from each other. The ability of the instruments that extend through sheath 100 to diverge from each other at the distal end may further assist the user in performing a medical procedure within the body.

Any feature that enables the instruments in the different lumens to diverge from each other may be used as diverging element 28. In some embodiments, the diverging element 28 may include a flexible section (such as a section made of a relatively more flexible material and/or having a smaller thickness) of elongate body 26 that can flex to enable the different instruments to separate from each other. In other embodiments, the diverging element 28 may include sections of the elongate body 26 having a variable flexibility. For instance, a section of the elongate body 26 proximate diverging element 28 may include balloons or cavities that may be selectively filled with air (or another fluid) to vary the flexibility in that region. As the balloons or cavities are filled, they also may enlarge, pushing the lumens 22, 24 away from one another if, for example, the balloon or cavity is between the lumens 22, 24. The balloons or cavities may be connected to a source of fluid located at the proximal end of the sheath 100, though a lumen extending through the sheath 100. In other embodiments, diverging element 28 may include sections of elongate body 26 in which the flexibility may be selectively varied thermally, electrically, or by another method. It is also contemplated that, in some embodiments, devices such as, for example, actuators may serve as the diverging element 28. Diverging element 28 may involve shapes or geometries to promote divergence. In some embodiments, the diverging element 28 may create one or more ramps adjacent to a lumen to guide an instrument in the lumen in a particular direction. In some embodiments, the diverging element 28 may be bubble shaped, spherical or hemi-spherically shaped features to allow instruments to glance off the diverging element 28 and be diverted relative to another instrument. In some embodiments, different diverging elements 28 may be associated with different lumens and may be positioned at different locations in sheath 100. The diverging element 28 may enable the distal ends of the instruments to diverge from each other and further assist in a medical procedure.

Figure 3A:
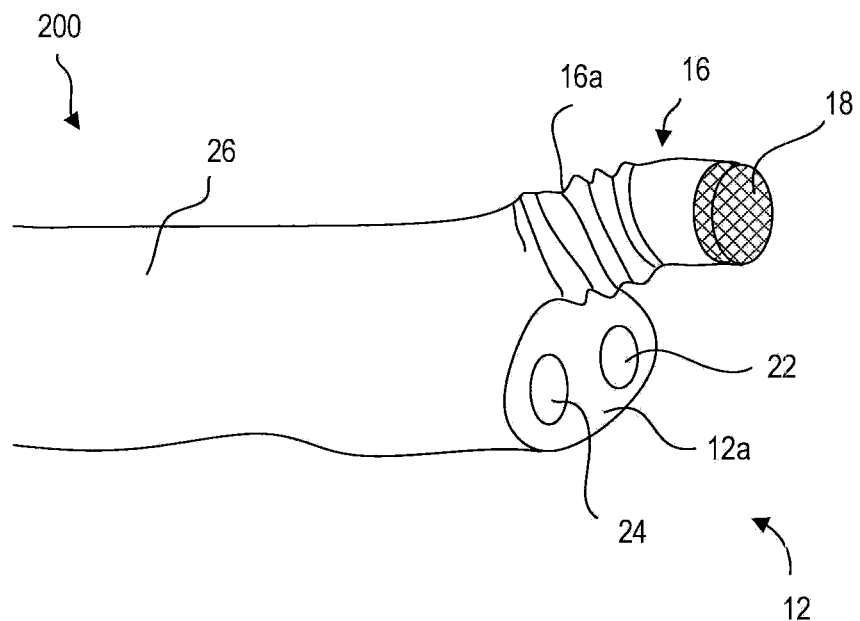
FIG. 3A is a schematic view of an exemplary embodiment of a sheath of the current disclosure.
Figure 3B:
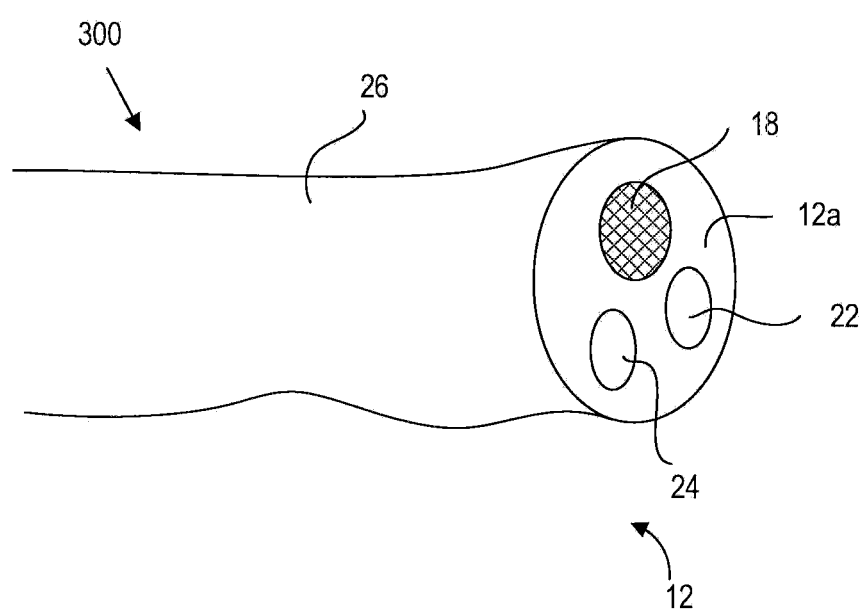
FIG. 3B is a schematic view of an exemplary embodiment of a sheath of the current disclosure.

In some embodiments, as illustrated in sheath 200 of FIG. 3A, the protruding neck region 16 may include an axially extendible section 16a similar to extendible section 27 of elongate body 26. Extendible section 16a may be configured to increase a length of the neck region 16 from a short length to a relatively longer length. In some embodiments, a reusable instrument in first lumen 20a may push against the viewing lens 18 positioned at a distal-most end of the neck region 16 to provide the force needed to axially extend the extendible section 16a. The extendible section 16a in the neck region 16 may allow for more accurate positioning of an imaging component relative to the treatment site and the end effectors of the tools inserted through the other lumens of the sheath 200. In some embodiments, as illustrated in sheath 300 of FIG. 3B, the neck region 16 may be eliminated. In such embodiments, the first lumen 20 may terminate at the distal face 12a, and the viewing lens 18 may be provided at the distal face 12a.

Although one sealed lumen (first lumen 20) and two open lumens (second lumen 20b and third lumen 20c) are illustrated in FIGS. 1A-3B, this is only exemplary. In general, any number of sealed and open lumens may be provided in a sheath of the current disclosure. Further, although these lumens are illustrated as being circular, in general, these lumens can have any cross-sectional shape. The cross-sectional shape may be fixed along the length or may vary along the length of elongate body 26. The change in cross-sectional shape along the length may be stepwise or continuous. In some embodiments, some or all lumens may be lined with a polymeric (or another) layer or coating (such as, for example, a lubricious coating) to facilitate use. In some embodiments, the lumens and the sheath 100 may have surface modifications (for example, bumps, ribs, etc.) to lessen friction. Further, the first, second, and third lumens 20, 22, 24 may be arranged in any pattern in sheath 200. In some embodiments, the first, second, and third lumens 20, 22, 24 may be arranged along a vertical axis, a horizontal axis, or arranged in another pattern, such as, for example, positioned at the vertices of a triangle as illustrated in sheaths 10, 100, and 200 of FIGS. 1A-3B. It should be noted that the lumens extending through a sheath of the current disclosure may be arranged in any pattern, without limitation.

Figure 4A:
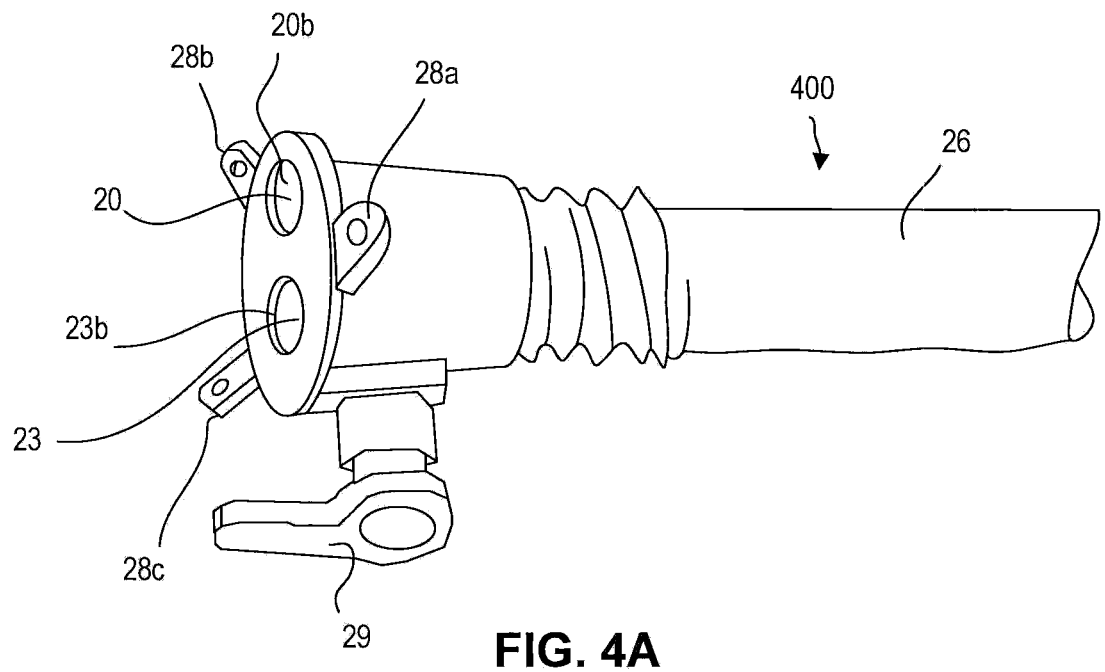
FIG. 4A is a schematic view of a proximal end of an exemplary sheath of the current disclosure.

With reference to FIG. 1, the proximal end 14 of sheath 10 may include openings 20b, 22b, and 24c that provide access to the first lumen 20, second lumen 22, and third lumen 24. Although a separate opening is described as providing access to each one of these lumens, in some embodiments, a single opening may provide access to multiple lumens. For example, in some embodiments, as illustrated in sheath 400 of FIG. 4A, a single opening 23b may provide access to the second and third lumens 22, 24. In such an embodiment, opening 23b may open to a lumen 23 that may branch into the second and third lumens 22, 24 at a location between the proximal and distal ends 14, 12. The proximal end 14 of sheath 100 may also include features, such as, for example, features 28a, 28b, 28c that mate with, or dock with, corresponding features of equipment that may assist in the surgical process. For example, the proximal end 14 of the sheath 10 may couple with equipment that may provide insufflation capabilities to the sheath 10. Lock 29 may assist in locking the proximal end 14 of sheath 400 with the insufflation or other equipment. In such an embodiment, insufflation may be provided through one or more lumens that extend through the sheath 10.

Figure 4B:
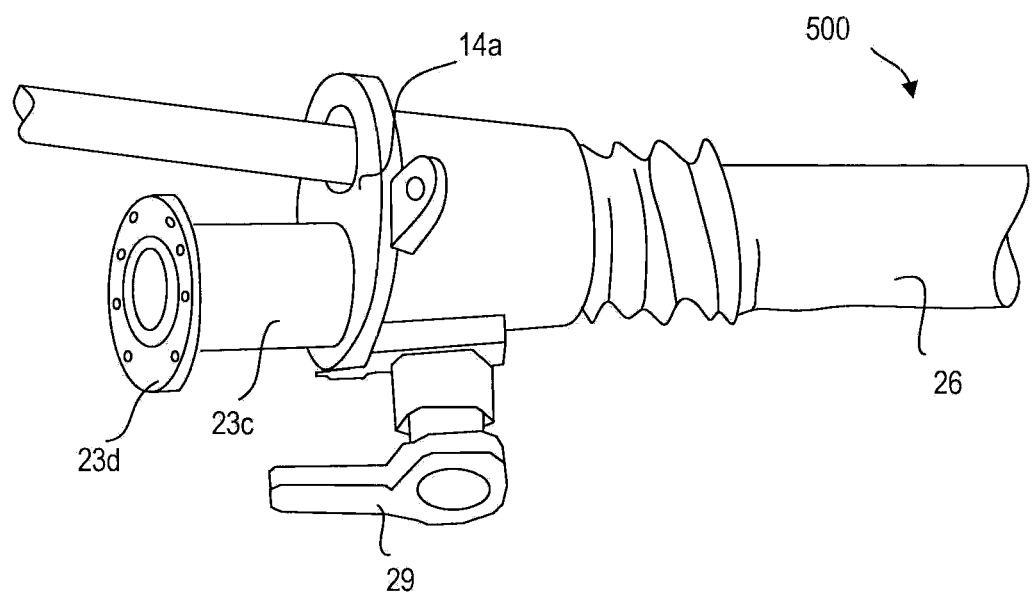
FIG. 4B is a schematic view of a proximal end of another exemplary sheath of the current disclosure.
Figure 4C:
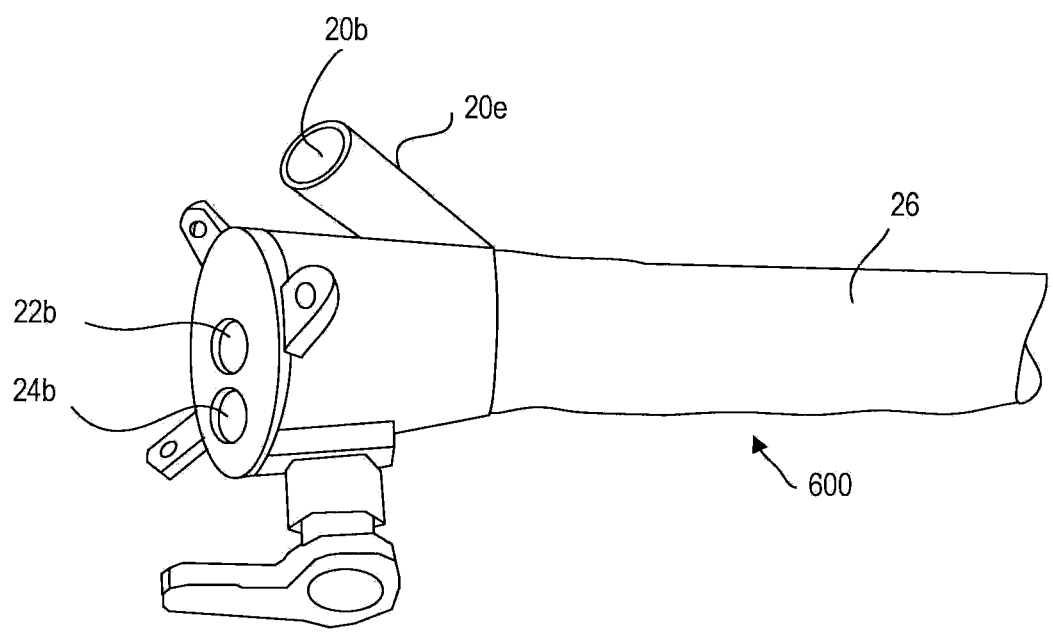
FIG. 4C is a schematic view of a proximal end of another exemplary sheath of the current disclosure.

In some embodiments, as illustrated in sheath 500 of FIG. 4B, one or more of these lumens may include projecting portions (such as, for example, 23c) that project past the proximal face 14a. The projecting portions may be flexible or rigid and some or all of these projecting portions may include seals (such as, for example, seal 23d) or other fixtures. In some embodiments, these projecting portions of the lumens may mate with equipment that may assist in the medical procedure. For example, in an exemplary medical procedure, second lumen 22 may be an irrigation lumen configured to facilitate fluid flow to a work site within the body, and the third lumen 24 may be an aspiration lumen configured to provide suction to the work site. In such an embodiment, the projecting portion 22c may include a lumen that is fluidly coupled to a fluid tank (or another source of fluid) and another lumen that may be fluidly coupled to a suction pump (or another device that provides suction). The seal 23d may assist in providing a fluid tight connection between the fluid source/suction pump and the corresponding lumen. In some such embodiments, the distal ends of the second and third lumens 22, 24 may also include devices that may assist in its functioning. For example, a nozzle (or another similar device configured to alter fluid flow) may be attached to the distal end 12 of second lumen 22 to assist in impinging the fluid at a desired location. Fluid may be directed to the work site through the second lumen 22 and suction may be provided through the third lumen 24 to remove the fluid (and/or biological material) from the work site. In this manner, a tissue sample may be extracted out of the body through the third lumen 24. In some embodiments (such as, for example in sheath 600 of FIG. 4C), a port 20e positioned between the proximal and distal ends 12, 14 of the sheath 600 may provide access to the first lumen 20. In some embodiments, port 20e may extend at an angle from a longitudinal axis of elongate body 26.

Any type of medical instrument known in the art may be provided through one or more lumens, for example, the second and the third lumens 22, 24. These medical instruments may be configured to perform specific tasks to assist in the desired medical procedure. In some cases, an end effector that is configured to perform the task may be coupled to an elongate member that extends into the body through the second and the third lumens 22, 24. The elongate member may operatively couple the end effector to an actuation device at the proximal end 14 to operate the end effector. Since the distal ends of the second and third lumens 22, 24 are open, the medical instruments directed into the body through these lumens may directly contact body tissue. Therefore, in some exemplary medical procedures using a disclosed sheath, these medical instruments may be sterilized or may be disposed (along with the sheath) after use.

Figure 5A:
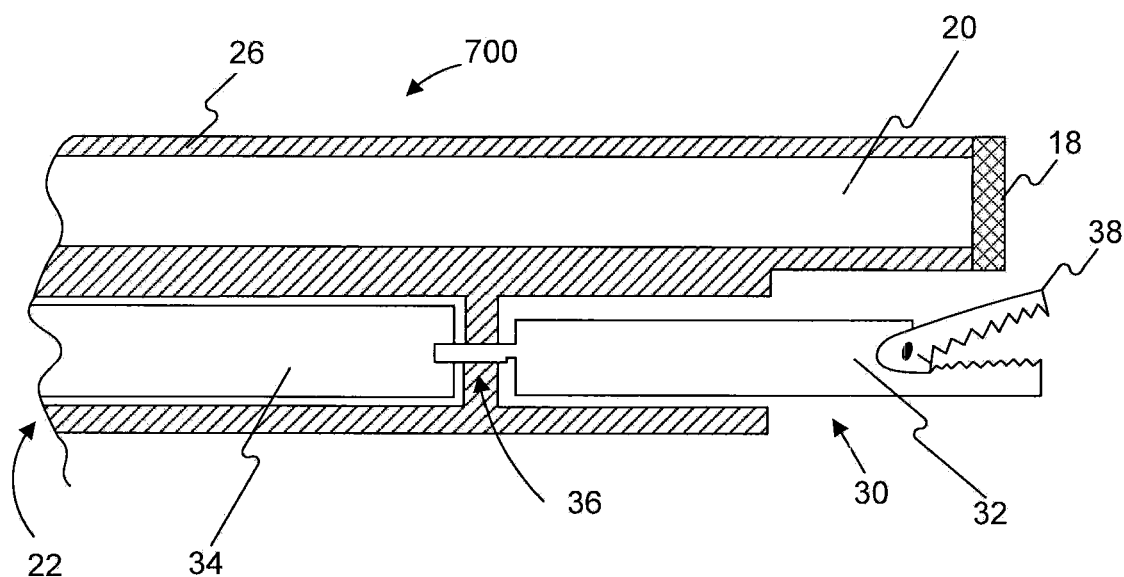
FIG. 5A is a schematic view of an exemplary sheath of the current disclosure having a medical instrument with disposable and reusable portions.

In some embodiments of a sheath of the current disclosure, a medical instrument directed through the second or third lumen 22, 24 may be only partially disposable with a remainder of the instrument being reusable. In these embodiments, a portion of the instrument that contacts body tissue may engage with a reusable portion of the instrument that is positioned within the sheath and isolated from body tissue. FIG. 5A illustrates one exemplary embodiment of sheath 700 having a disposable portion 32 preloaded to the distal end 12 thereof. The disposable portion 32 may include an end effector 38 at its distal end, and may mate with a reusable portion 34 that extends through the second lumen 22 of the sheath 700. The disposable and reusable portions 32, 34 together form the instrument 30. The reusable portion 34 may join with the disposable portion 32 at an interface 36 within the sheath 700. The interface 36 may include features configured to transmit relative motion and/or signals between the coupled reusable and disposable portions 34, 32 to enable the end effector 38 (at the distal end of the disposable portion 32) to be controlled by an actuation device at the proximal end of the reusable portion 34. The interface 36 may also be configured to prevent biological tissue from contacting the reusable portion 34 within the sheath 700. In some embodiments, the interface 36 may also be configured to prevent or minimize biological fluids from entering the sealed portion of the second lumen 22 that contains the reusable portion 34 of instrument 30. In some embodiments, the sheath 700 may be thickened at selected regions to better seal the second lumen 22. In some embodiments, the disposable portion 32 may pierce through a seal a distal end of the second lumen 22 to interface with a distal end of the reusable portion 34 extending through the second lumen 22. The seal may be remain functional to prevent or minimize the flow of biological fluids from entering the second lumen 22.

Figure 5B:
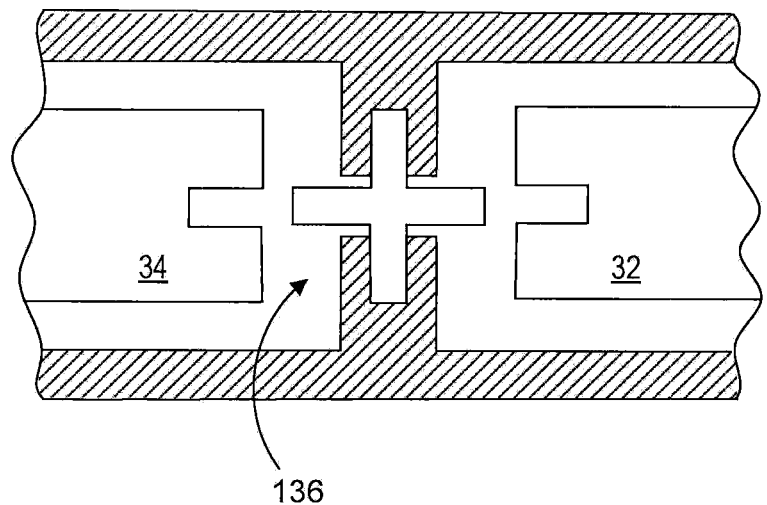
FIG. 5B is an exemplary interface between the disposable and reusable portions of the medical instrument of FIG. 5A.

Any type of interface that enables the disposable and reusable portions 32, 34 to be coupled together while isolating the reusable portion 34 from body tissue may be used as interface 36. Interface 36 may be an integral part of one of the portions (such as, for example, an integral part of the disposable portion 32 as illustrated in FIG. 5A), or may be a part of the sheath 700. FIG. 5B illustrates an exemplary interface 136 that is part of the sheath. In such an embodiment, the disposable and reusable portions 32, 34 of the instrument 30 may be separately coupled to the interface 136. In an embodiment using an instrument 30 with disposable and reusable portions 32, 34, the sheath 700 along with the disposable portion 32 may be disposed after use while the reusable portion 34 may be reused. In general, any portion of an instrument can be the reusable portion 34. For instance, in some embodiments, only a portion of the end effector 38 may be disposable while the remaining portions of the instrument 30 may be reusable. In other embodiments, only a portion of the actuation device may be reusable while the remaining portions of the instrument 30 may be disposable.

In some exemplary medical procedures using an instrument 30 with disposable and reusable portions 32, 34, the two portions may be first coupled together before the sheath 700 is inserted into the body. In other embodiments, only one of the portions (such as for example, the disposable portion 32) may be coupled to the sheath 700 before the sheath 700 is inserted into to the body. The remaining portion (such as, for example, the reusable portion 34) may be coupled after the sheath 700 is inserted into to the body.

Figure 6A:
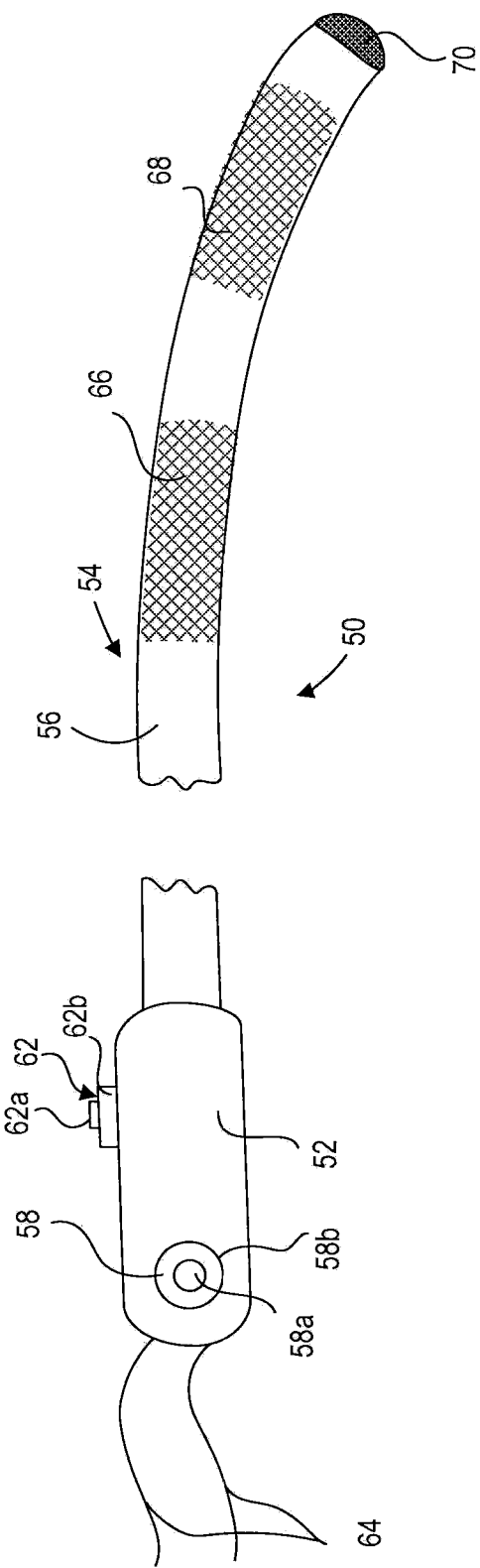
FIG. 6A is a schematic view of an exemplary reusable medical instrument that may be used with a sheath of the current disclosure.

FIG. 6A illustrates a reusable instrument 50 that may directed into the body though a sealed first lumen 20 of a disclosed sheath (for example, sheath 10 of FIG. 1). Any instrument (such as, for example, a light wand, an imaging device, an endoscope, etc.) may serve as the reusable instrument 50. The reusable instrument 50 may include a flexible elongate section 56 extending from a handle 52. The handle 52 may include controls 58, 62 that may activate different features of the reusable instrument 50. The elongate section 56 may include one or more bendable sections, such as, for example, a first bendable section 66 and a second bendable section 68, positioned along its length. These bendable sections 66, 68 may be configured to bend or deflect in response to the actuation of the controls 58, 62 and have a curved disposition. In some embodiments, one of these controls (such as, for example, control 58) may actuate the first bendable section 66 and the other control (such as, for example, 62) may actuate the second bendable section 68. Other embodiments of reusable instruments may be controlled in a different manner. For example, in some embodiments, control 58a may be actuated to deflect the first bendable section 66 along a horizontal axis (that is, left/right) and control 58b may be actuated to deflect the second bendable section 68 along a horizontal axis. Similarly, controls 62a and 62b may actuate the first and second bendable sections 66, 68, respectively, along a vertical axis (up/down). These controls may actuate the bendable sections in any manner. In some embodiments, these controls may, mechanically, thermally, or electrically actuate the bendable sections to deflect in a desired direction. In other embodiments, the bendable sections may incorporate features (such as a fluid cavity, etc.) or devices (such as, actuators) that assist in the deflection of the elongate section 56 in a desired direction. Cables 64 (or conduits) may direct signals (and/or fluids) to the reusable instrument 50 to assist in the deflection of the bendable sections. In some embodiments, dynamic materials (such as, for example, shape memory materials, electroactive materials, etc.) may be used to actuate one or more bendable sections of the reusable instrument 50.

The distal-most end of elongate section 56 may include an optical element 70 that may receive and/or transmit light. Any device (such as, a light source, imaging device, etc.) that may emit light and/or may operate using received light may serve as the optical element 70. For example, optical element 70 may include a camera, imaging sensor (such as, for example, a Complementary Metal Oxide Semiconductor, or a CMOS sensor, Charge Coupled Device, etc.), or another image receiving device (such as, for example, a fiber optic imaging device). Optical element 70 may transmit an image signal to a monitor or other display device positioned outside the body and viewable by the user. The image signals may correspond to still pictures and/or transient images that display time varying images of the work site within the body. In some embodiments, optical element 70 may transmit the image signals wirelessly, while in other embodiments, wires or cables embedded in the reusable instrument 50 may be used to transit these image signals. It is also contemplated that, in some embodiments, control signals may also be transmitted to the optical element 70 from outside the body, wirelessly or through the cables embedded in the reusable instrument 50. Additionally or alternatively, optical element 70 may also include an illumination device that is configured to illuminate the work site. The illumination device may include, among others, bulbs, LEDs, fiber optic cables and light guides. In some embodiments, the second bendable section 68 may be positioned proximate the optical element 70 and the first bendable section 66 may be positioned proximal to the second bendable section 68.

Figure 6B:
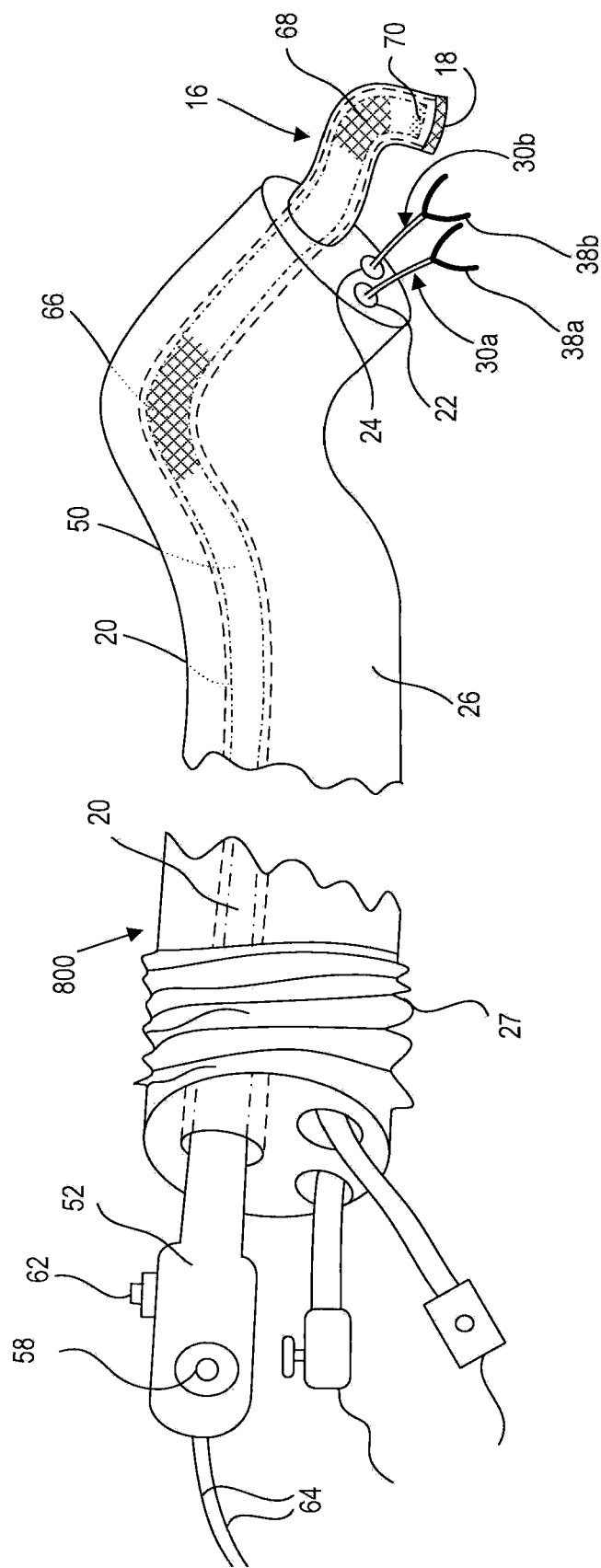
FIG. 6B is a schematic illustration of the reusable medical instrument of FIG. 6A used with an embodiment of a sheath of the current disclosure.

FIG. 6B illustrates an embodiment of sheath 800 with a reusable instrument 50 extending through a first lumen 20 and two disposable instruments 30a, 30b extending through the second and third lumens 22, 24, respectively. The reusable instrument 50 may be extended through the first lumen 20 to position the optical element 70 proximate the viewing lens 18. When the reusable instrument 50 is thus positioned, in some embodiments, the second bendable section 68 of the reusable instrument 50 may be positioned in the neck region 16 of the sheath 800. In this configuration, actuating the second bendable section 68 to deflect this region of the reusable instrument 50 may be used to position the viewing lens 18 and the optical element 70 in any manner suited to view and/or illuminate the work site (such as, for example, in an orientation suited to obtain an elevated view of the work site). Actuating the second bendable section 68 may also be used to guide or steer the sheath 800 and the instruments 30a, 30b extending through the second and third lumens 22, 24 to the work site. Actuating the first bendable section 66 may also be used to guide and position the distal end 12 of the sheath 800 in a desirable manner within the body. Used together, the first and second bendable sections 66, 68 may be used to position the sheath 800, and the instruments therein, in a desirable manner within the body. For example, the first bendable section 66 may be actuated to raise the distal end 12 of sheath 800 off the patients anatomy and the second bendable section 68 may be actuated to steer and direct the instruments to a desired location and position the optics in a manner most suited to visualize and/or illuminate the work site. Thus, a sheath of the current disclosure may be used to attach an optics lumen to a standard flexible disposable instrument. The sheath may also be used to provide steering capability to a standard non-articulating instrument by the use of a steerable instrument (such as, for example, an endoscope) in the sheath.

Sheath 10 (see FIG. 1) may be affixed to an instrument (reusable instrument 50 or disposable instrument 30) in any manner. In some embodiments, an instrument may be slid into (or squeezed into) a lumen of the sheath 10, while in other embodiments, the sheath 10 may be slid over the instrument. It is also contemplated that the sheath may be rolled over an instrument (similar to a condom), wrapped, zip-locked, hook and looped (such as, by using a Velcro® like attachment mechanism), adhered or expanded on the instrument. Expanding the sheath 10 on an instrument may include reversibly expanding the sheath 10 (by, for example, inflating with air or another fluid, by using temperature or a chemical change to increase or decrease the size of a lumen, etc.) to insert an instrument through the lumen and then contracting the lumen. In some embodiments, the instrument may be attached to the sheath 10 using features such as mechanical ties, "0" rings, clamps, etc.

The sheath may be attached to an instrument in any order without limitation. For example, in some exemplary medical procedures, all the instruments (reusable instrument 50 and disposable instrument 30a, 30b, etc.) may be first inserted (or attached to the sheath by using another one or the procedures described above) into the sheath 10 and the extendible section 27 extended, before the sheath 10 (along with the inserted instruments) is inserted into the body of the patient. In other embodiments, only some of the instruments may be inserted into the sheath 10 before the sheath 10 is inserted into the body. The other instruments may be inserted into the sheath 10 after the sheath 10 is within the body. For example, a reusable medical instrument 50 may first be inserted into the sheath 10 before the sheath 10 is inserted into the body of the patient. Pushing the reusable instrument 50 into the sheath 10 may extend the extendible section 27 and the length of the sheath 10. Disposable instruments 30a, 30b, etc. may be inserted into the second and third lumens 22, 24 of the sheath 10 after the sheath is in the body. It is also contemplated that, in some exemplary medical procedures, one or more instruments may be first inserted into the body before the sheath 10 is slid over these instruments. Other instruments may then be inserted thorough the lumens of the sheath. It is also contemplated that, in some embodiments, the sheath 10 may be first inserted into the body before the instruments are inserted into their respective lumens. In some embodiments, a seal may be formed around portions of the disposable instruments to prevent or minimize the entry of biological fluids into the sheath 10.

Figure 7:
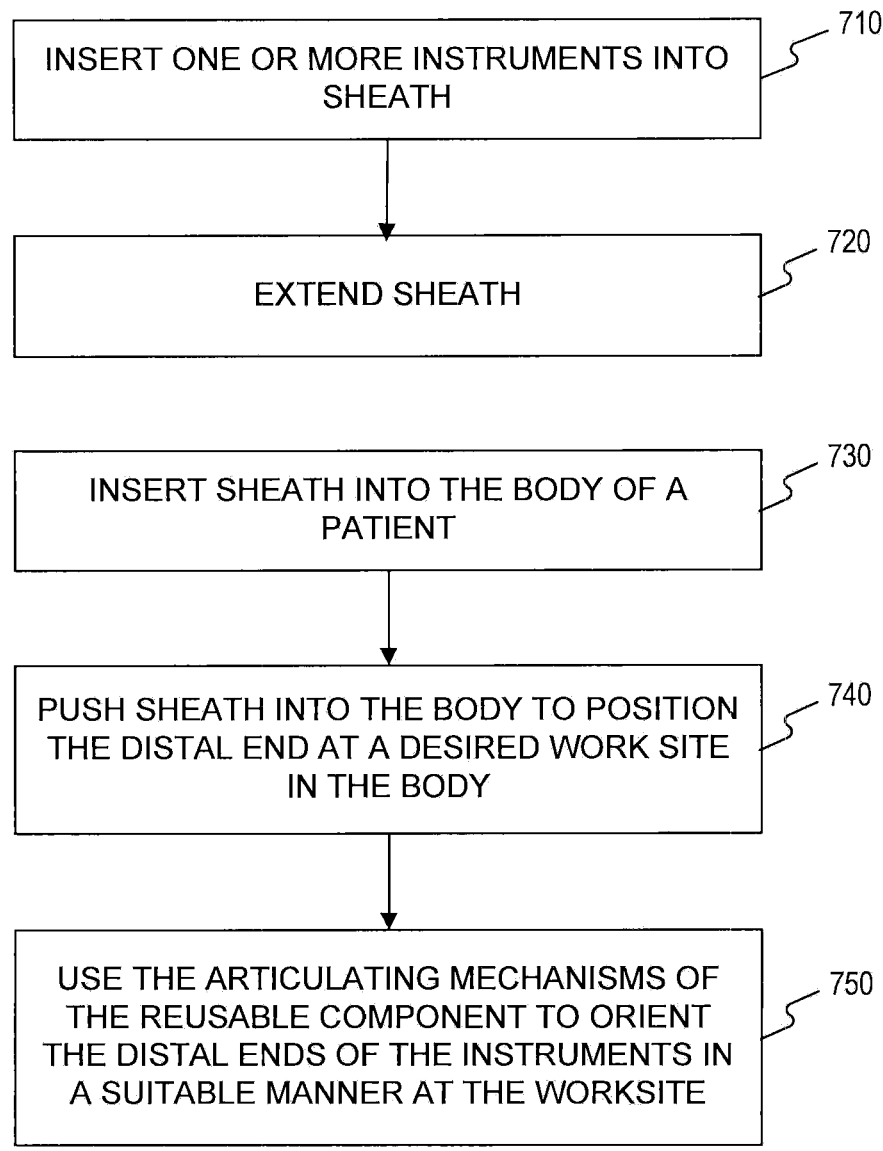
FIG. 7 is a flow chart illustrating an exemplary medical procedure using a sheath of the current disclosure.

FIG. 7 is a flow chart that illustrates an exemplary method of using a sheath (for example, sheath 10 of FIG. 1) of the current disclosure. As illustrated in FIG. 7, a reusable instrument 50 may be inserted into a closed lumen 20 of sheath 10 (step 710). The reusable instrument 50 may be pushed into the sheath 10 to extend the sheath 10 from a relatively short length to a longer length. One or more disposable medical instruments (30a, 30b, etc.) may be also be inserted into one or more open lumens 22, 24 of the sheath 10. In some embodiments, a seal may be formed around portions of the disposable medical instruments to keep biological fluids from entering selected regions of the sheath 10. Although these instruments are described as being inserted into the sheath 10, as discussed above, these instruments may be attached in any manner to sheath 10. The sheath 10, along with the instruments, therein may then be inserted into the body of a patient (step 730). It is also contemplated that the sheath 10 may extended as the sheath 10 (along with the instruments therein) is inserted into the body. The sheath 10 may be inserted into the body through a natural anatomic opening or through an incision on the body of the patient. The sheath 10 may be pushed into the body to a work site within the body (step 740). The articulating mechanisms (such as, the first and/or second bendable sections 66, 68) of the reusable instrument 50 may be activated to steer and guide the sheath through the body and position the distal end 12 of the sheath 10, the viewing lens 18, and the end effectors 38a, 38b in a desired configuration at the work site (step 750). In some embodiments, the neck region 16 of the first lumen 20 may be manipulated to position the viewing lens 18 over the work site to get an elevated view of the work site. Although in the description above, the instruments are described as being inserted into the sheath 10 before the sheath 10 is inserted into the body, as described previously, this is only exemplary and in other embodiments, sheath 10 (alone or with some instruments inserted therein) may be inserted into the body before the instruments are inserted into the sheath 10. It is also contemplated that, in some embodiments, the sheath 10 may be extended after the distal end 12 of the sheath is positioned at the treatment site.

The embodiments described herein are exemplary only, and it will be apparent to those skilled in the art that various modifications and variations can be made in the disclosed systems and processes without departing from the scope of the invention. Other embodiments of the invention will be apparent to those skilled in the art from consideration of the specification and practice of the invention disclosed herein. It is intended that the specification and examples be considered as exemplary only, with a true scope of the invention being indicated by the following claims.

What is claimed is:

1. A sheath, comprising:
   a member extending from a proximal end to a distal end;
   a distally facing face located at the distal end of the member;
   a neck region extending distally beyond the distal end from the distally facing face;
   a first lumen extending from the proximal end of the member, beyond the distal end of the member, and within the neck region; and
   a second lumen extending from the proximal end of the member to the distally facing face;
   wherein the member includes a first extendible section configured to axially extend and contract between a first length and a second length, greater than the first length, to position the neck region and the distally facing face; and
   wherein the neck region includes a second extendible section configured to axially extend and contract between a third length and a fourth length, greater than the third length.

2. The sheath of claim 1, wherein the neck region is fixed to the distally facing face.

3. The sheath of claim 1, wherein a diameter of the neck region is less than a diameter of the distally facing face.

4. The sheath of claim 1, further comprising a third lumen extending from the proximal end of the member to the distally facing face.

5. The sheath of claim 4, wherein the second lumen and the third lumen diverge from each other at a distal region of the member.

6. The sheath of claim 1, wherein the first lumen is sealed at a distal end of the first lumen.

7. The sheath of claim 6, wherein the first lumen is sealed with a transparent window at the distal end of the first lumen.

8. The sheath of claim 1, wherein the second lumen is open at the distally facing face.

9. A sheath, comprising:
   a member extending from a proximal end to a distal end, wherein the member includes a distally facing face located proximal to the distal end;
   a first lumen extending from the proximal end to the distal end;
   a second lumen extending from the proximal end to the distally facing face; and
   at least two extendible portions of the member separated from each other by a non-extendible portion of the member, wherein each of the extendible portions has a variable axial length, wherein a first extendible portion of the at least two extendible portions is located distal to the distally facing face, and wherein extending a second extendible portion of the at least two extendible portions axially positions the distally facing face further from the proximal end of the member, and axially extends and contracts the member between a first length and a second length, greater than the first length.

10. The sheath of claim 9, wherein the first lumen extends through the first extendible portion.

11. The sheath of claim 9, wherein a distal region of the member located distal to the distally facing face has a diameter that is less than a diameter of a region of the member located proximal to the distally facing face.

12. The sheath of claim 9, wherein the first lumen is sealed at a distal end of the first lumen.

13. The sheath of claim 9, wherein the second lumen is open at a distal end of the second lumen.

14. The sheath of claim 13, further comprising a third lumen extending from the proximal end to the distally facing face, wherein the third lumen is open at a distal end of the third lumen.

15. The sheath of claim 14, wherein a distal region of the second lumen and a distal region of the third lumen diverge from one another proximal to the distally facing face.

\* \* \* \* \*